US010028801B1

(12) United States Patent
McGinley et al.

(10) Patent No.: US 10,028,801 B1
(45) Date of Patent: Jul. 24, 2018

(54) OFFSET REFERENCE GUIDE FOR ORTHOPEDIC SURGICAL APPLICATIONS

(71) Applicant: McGinley Engineered Solutions, LLC, Casper, WY (US)

(72) Inventors: Joseph C. McGinley, Casper, WY (US); Vincent Palazzolo, Casper, WY (US)

(73) Assignee: McGinley Engineered Solutions, LLC, Casper, WY (US)

( * ) Notice: Subject to any disclaimer, the term of this patent is extended or adjusted under 35 U.S.C. 154(b) by 0 days.

(21) Appl. No.: 15/561,469

(22) PCT Filed: Mar. 29, 2017

(86) PCT No.: PCT/US2017/024796
§ 371 (c)(1),
(2) Date: Sep. 25, 2017

(87) PCT Pub. No.: WO2017/172949
PCT Pub. Date: Oct. 5, 2017

Related U.S. Application Data

(60) Provisional application No. 62/316,209, filed on Mar. 31, 2016.

(51) Int. Cl.
*A61B 5/00* (2006.01)
*G01B 3/04* (2006.01)
*A61B 90/00* (2016.01)
*A61B 17/86* (2006.01)

(52) U.S. Cl.
CPC .............. *A61B 90/06* (2016.02); *A61B 17/86* (2013.01); *G01B 3/04* (2013.01); *A61B 2090/061* (2016.02)

(58) Field of Classification Search
CPC .............. A61B 90/06; A61B 2090/061; A61B 2090/062; G01B 3/04
USPC ................................ 33/545, 679.1, 549, 712
See application file for complete search history.

(56) References Cited

U.S. PATENT DOCUMENTS

| 1,287,040 A | * | 12/1918 | Junker | G01B 3/166 |
| | | | | 235/61 B |
| 1,375,747 A | * | 4/1921 | Zigray | G01B 3/20 |
| | | | | 33/679.1 |
| 1,860,174 A | * | 5/1932 | Cronk | G01B 3/00 |
| | | | | 33/403 |
| 2,981,005 A | * | 4/1961 | Moe | G01B 3/14 |
| | | | | 33/555.1 |
| 3,230,628 A | | 1/1966 | Hite | |

(Continued)

Primary Examiner — Christopher Fulton
(74) Attorney, Agent, or Firm — Marsh Fischmann & Breyfogle LLP

(57) ABSTRACT

An offset reference guide for use in determining an offset value for orthopedic fasteners to be used with surgical hardware. The reference guide may include a reference surface against which the surgical hardware may be disposed. In turn, an orthopedic fastener may be inserted through a fastener hole of the surgical hardware and accepted by a fastener relief of the guide. Upon fully seating the orthopedic fastener relative to the surgical hardware, the distal end of the orthopedic fastener may align with one of a set of offset indicia calibrated relative to a known length of the orthopedic fastener. In turn, an offset value for the surgical hardware may be determined that may, for example, be used to augment measurements of bore lengths taken for a bore into which an orthopedic fastener is to be disposed.

20 Claims, 14 Drawing Sheets

(56) References Cited

U.S. PATENT DOCUMENTS

| | | | |
|---|---|---|---|
| 5,309,648 | A | 5/1994 | Allard |
| 5,501,020 | A | 3/1996 | Welt |
| 6,780,115 | B2 | 8/2004 | Schmieding |
| 7,111,411 | B2 | 9/2006 | Knopfle |
| 2009/0088767 | A1* | 4/2009 | Leyden .............. A61B 17/1721 606/96 |

* cited by examiner

OFFSET REFERENCE GUIDE FOR ORTHOPEDIC SURGICAL APPLICATIONS

RELATED APPLICATIONS

This application is a U.S. National Stage Application under § 371 of PCT Application No. PCT/US17/024796, entitled OFFSET REFERENCE GUIDE FOR ORTHOPEDIC SURGICAL APPLICATIONS", filed on Mar. 29, 2017, which claims the benefit of U.S. Provisional Patent Application No. 62/316,209 filed Mar. 31, 2016, entitled "OFFSET REFERENCE GUIDE FOR ORTHOPEDIC SURGICAL APPLICATIONS," which is incorporated herein by reference in its entirety.

BACKGROUND

Orthopedic surgery often involves installation of surgical hardware. For instance, orthopedic surgical hardware may include plates, braces, implants, or other fixtures. These hardware portions may be used in a variety of wide ranging contexts in orthopedic surgery. For instance, such hardware may be introduced to stabilize fractures, provide traction, or be utilized in other potential applications.

Installation of such hardware often includes affixing the hardware to a bone by way of orthopedic fasteners such as screws, bolts, pins, or the like. In turn, orthopedic tools such as drills, reamers, saws, drivers, and other instruments have been developed to assist in affixing orthopedic hardware to a bone. For example, when affixing hardware to a bone, pilot holes or other bores may be drilled though a bone to which the hardware is to be attached prior to securing the hardware to the bone using fasteners. As each individual patient's bone structure may be unique, the length of the bore may be measured to determine the correct fastener to be used such that the fastener extends through as much of the bore as possible without extending beyond the distal boundary of the bore.

A number of orthopedic hardware suppliers provide hardware and/or related fasteners for use in orthopedic surgeries. Each of these hardware suppliers may provide varying configurations and/or sizes of hardware. In turn, orthopedic hardware suppliers may provide kits that include the components related to the hardware to be utilized. For instance, the fasteners that accompany the hardware may be specifically related to the hardware supplier. As such, orthopedic hardware suppliers often provide depth gauges and other accompanying tools (e.g., including powered surgical instruments) in such a kit for use with the hardware supplied by the given supplier.

SUMMARY

In view of the foregoing, it is recognized in the present disclosure that facilitating determination of an offset value for given surgical hardware may provide certain advantages. For example, oftentimes surgical hardware may be provided in a kit that may include the hardware, fasteners for affixing the hardware to a bone, a depth gauge that may be utilized to determine fastener lengths, and/or instruments (e.g., drill bits or fastener drivers). These kits may be calibrated such that the kit is designed to be used as a comprehensive system for use with the surgical hardware.

However, users (e.g., surgeons) may wish to interchange portions of the kit associated with the surgical hardware. Such desire to interchange parts may be driven based on cost advantages, personal preferences, particular operational requirements, or other motivations. In any regard, when interchanging or using components external to the kit, the existing components of the kit may not be standardized to a clear universal standard. This may be particularly evident in the length of the fasteners provided with the kit. For example, a kit's fasteners and depth gauges may be calibrated such that the determination of a fastener length determined by the depth gauge of the kit may dictate fastener selection from the kit. Specifically, a kit may include a depth gauge and corresponding fasteners that are calibrated to account for an offset value of the hardware such that the value of the offset value is not evident to the user when employing the kit.

For instance, a depth gauge for a kit, when measuring a "bone to bone" bore length (i.e., the actual distance from the beginning of the bore to the end of the bore), may read "10 mm" indicating a 10 mm long bore. However, the depth gauge may be calibrated to account for an offset value such that the actual bore length may vary from 10 mm. If, for instance, a 2 mm offset value is "built in" to the depth gauge, the bore may actually only be 8 mm in length for the actual bone to bone length. Similarly, if an external depth gauge is used to measure a bore length of 10 mm, use of a "10 mm" long fastener may be selected from the kit. However, the actual fastener length may vary from the "10 mm" indication. For example, the fastener length indication may be calibrated relative to the hardware such that a "10 mm" fastener is actually longer than indicated to accommodate the hardware offset value. Accordingly, if a depth gauge external to the kit or fasteners external to the kit were used, the coordinated calibration of the components may be interrupted and discrepancies may occur. Different kits may build this offset value in differently. As such, the offset value for a given surgical hardware component may not be evident to the surgeon and may prevent the interchanging of components external to the kit.

In this regard, determination of an offset value for a given surgical hardware component may allow for interchangeable use of components external to a provided kit, which may be desired based on the discussion presented above. That is, determination of an offset value may allow for use of external depth gauges and/or fasteners sourced external from a kit. For instance, convenient and efficient instruments for determination of a bore length have been developed that may be advantageously used in lieu of a depth gauge provided with a kit. Examples of such instruments are described in U.S. Pat. No. 6,665,948; U.S. Pat. No. 9,204,885; U.S. patent application Ser. No. 14/018,252; U.S. patent application Ser. No. 14/537,585; U.S. patent Ser. No. 14/614,107; U.S. patent application Ser. No. 14/845,602; U.S. Prov. App. No. 62/247,022; and U.S. Prov. App. No. 62/247,025; each of which are co-owned with the present application and each of which is incorporated by reference in their entirety herein. By determining an offset value for hardware, such conventional depth gauges may be used in conjunction with the determined offset value to allow greater flexibility to users.

Specifically discussed in the present disclosure is an offset reference guide that may be utilized for determining an offset value for orthopedic surgical hardware. Such a guide may be used by a user (e.g., a surgeon) to determine the offset value to, for example, overcome limitations in orthopedic hardware kits provided with coordinated calibration between components.

Accordingly, a first aspect includes an offset reference guide for use in determining offset values for orthopedic surgical hardware. The guide includes a reference surface adapted to contactably engage a surgical hardware component at an interface surface of the surgical hardware component. The guide also includes a gauge surface extending relative to the reference surface. The gauge surface is visible to a user of the guide. The guide also includes a fastener relief extending from the reference surface and relative to the gauge surface. The fastener relief is configured to receive and index an orthopedic fastener relative to the reference surface and the gauge surface when the orthopedic fastener is disposed through a surgical hardware component disposed at (e.g., in contact with) the reference surface. The guide further includes offset indicia disposed on the gauge surface and aligned with the fastener relief. The offset indicia are indicative of an offset to at least one known fastener length relative to the fastener relief.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For instance, in an embodiment, a first portion of the fastener relief may include a bore extending along at least a first end portion of the fastener relief adjacent to the reference surface (e.g., adjacent to a terminal end portion of the fastener relief adjacent to the reference surface). The bore may be sized to receive the orthopedic fastener therein. Furthermore, the guide may include a second portion of the fastener relief that may include a channel having an open portion along at least a portion of the gauge surface such that the fastener is visible relative to the gauge surface along the second portion. In turn, the bore may assist in aligning and indexing a fastener introduced into the fastener relief and the channel may allow for a distal portion of the fastener to be visible in relation to the gauge surface and the offset indicia disposed thereon. The bore and the channel may be collinear to accept a fastener through both the first portion and the second portion.

Additionally, the reference surface may be configured to promote intimate, flush contact between the hardware and the reference surface to assist in accuracy in determining an offset value. Accordingly, the reference surface may be radiused relative to a terminal end portion of the fastener relief. Specifically, a radius of curvature of the reference surface may be smaller than the radius of curvature of an interface surface of a surgical hardware component disposed at the reference surface. In turn, the reference surface may present a convex surface that may engage a correspondingly concave surface of the hardware. As the radius of curvature of the reference surface may be smaller than a radius of curvature of the hardware, the reference surface may directly contact at least a portion of the hardware surrounding a fastener hole without bridging or other gapping occurring between the reference surface and the interface surface of the hardware.

In an embodiment, the reference surface may be contoured so as to have a complex profile that includes curvature in a number of dimensions. For example, the reference surface may be contoured about the terminal end portion of the fastener relief such that the reference surface comprises a first and second radius of curvature relative to two axes, respectively, that are each orthogonal to the fastener relief. In this regard, the reference surface may have a curvature profile that extends relative to the terminal end portion of the fastener relief so as to accommodate intimate contact with a hardware component. The first and second radiuses of curvature that extend in different directions relative to the fastener relief may be different such that different ones of the profiles created by the different radiuses of curvature may accommodate different interfaces surfaces for different hardware components.

In an embodiment of an offset reference guide, the guide may include a plurality of fastener reliefs. Each of the plurality of fastener reliefs may extend from the reference surface and relative to the gauge surface. The plurality of fastener reliefs may each extend a different distance along the gauge surface. As such, each of the plurality of fastener reliefs may correspond to a different known fastener length such that each of the plurality of fastener reliefs may include a corresponding offset indicia for the corresponding known fastener length of the given fastener relief. In turn, any one of a number of different known fastener lengths for fasteners (e.g., any one of a number of fasteners provided by a kit accompanying the orthopedic hardware) may be used by selecting a corresponding one of the plurality of fastener reliefs for use in determining the offset value.

In another embodiment, a plurality of offset indicia may be provided that each correspond to a different known fastener length. The plurality of offset indicia may be disposed relative to the fastener relief. In this regard, only one fastener relief may be provided. In this embodiment, a given one of the plurality of offset indicia may be used for a known fastener length for a fastener disposed in the single fastener relief. That is, the single fastener relief may be used regardless of the fastener length with the known fastener length resulting in selection of a corresponding one of the offset indicia for determining the offset value.

Furthermore, embodiments of the offset reference guide may include one or more grip portions extending relative to the gauge surface. The one or more grip portions may assist in securely holding the guide when moving the guide. For instance, a plurality of grip portions may be disposed at opposite end portions of the offset reference guide. The grip portions may comprise fins extending from a rear surface of the offset reference guide. This may allow for a user's hand to wrap around the grip portion to securely grasp the grip portion to move and/or manipulate the guide.

The offset reference guide may also include one or more supports that support the guide when disposed on the surface. The one or more supports may be provided by the one or more grip portions. As such, in an embodiment, grip portions comprise support structures disposable on a surface. The support structures may orient the gauge surface at an angle relative to the surface for viewing by a user of the offset reference guide.

The offset reference guide may be adapted for use in a surgical context. Accordingly, the offset reference guide may itself be made sterile so that the offset reference guide may be introduced into a sterile surgical field. Accordingly, the offset reference guide may comprise a stainless steel or other metal that may be capable of being autoclaved or otherwise sterilized. As such, upon introduction into a sterile surgical field, the offset reference guide may contact surgical hardware components and fasteners and maintain the sterility of the components.

A second aspect includes a method for use of an offset reference guide in determining offset values for orthopedic surgical hardware. The method may include positioning an interface surface of a surgical hardware component in contact with a reference surface of the offset reference guide. The method further includes aligning a fastener hole of the surgical hardware component with a fastener relief of the offset reference guide and inserting an orthopedic fastener of a known length through the fastener hole of the surgical hardware component relative to the fastener relief to dispose the orthopedic fastener relative to a gauge surface along which the fastener relief extends. In turn, the method also includes reading an offset value from offset indicia disposed on the gauge surface and aligned with the fastener relief. The offset value corresponds to a given one of the offset indicia with which a distal end of the orthopedic fastener is aligned when disposed in the fastener relief.

A number of feature refinements and additional features are applicable to the second aspect. These feature refinements and additional features may be used individually or in any combination. As such, each of the following features that will be discussed may be, but are not required to be, used with any other feature or combination of features of the second aspect. For instance, the offset guide of the method of the second aspect may be according to any of the description provided above in relation to the first aspect.

Additionally, the method may further include selecting, from a plurality of fastener reliefs each corresponding to a different respective known fastener length, a given fastener relief for inserting the orthopedic fastener based on the known length of the orthopedic fastener. Accordingly, and as described above, any one of a number of fasteners of a known length may be selected for use in determining an offset value for the hardware. Upon selection of a given known fastener length, a corresponding fastener relief may be selected for insertion of the fastener to determine the offset value for the hardware.

In an embodiment, the method may include use of the determined offset value in connection with affixing the hardware to a bone. In turn, the method may also include measuring a measured bore length of a drilled hole through a bone to which the surgical hardware is to be affixed and adding to the measured bore length the offset value to obtain a corrected fastener length. The method may further include selecting a fastener based on the selected fastener length. For instance, the selection of the fastener may include selecting a fastener from a kit provided with the orthopedic hardware based on the corrected fastener length based on the measured bore length and the offset value.

In an embodiment, the inserting may include fully distally seating the orthopedic fastener in the fastener relief relative to the surgical hardware. For instance, the fastener hole of the hardware may include contouring including beveling or chamfering that may result in a head of the fastener residing at a given position of the hardware. Fully seating the fastener distally may mimic the position of the fastener when installed relative to the bone, thus improving the accuracy of the offset value determined using the offset reference guide.

As may be appreciated, in some applications, surgical hardware may include a plurality of fastener holes through which fasteners are disposed when installed relative to a bone of a patient. In some of these applications, the offset for the hardware may be the same for each of the fastener holes such that a single offset value, once determined, may be used in conjunction with selection of a fastener for each of the plurality of holes. In other applications, the offset values for each fastener hole may differ for given hardware.

In such instances where the offset value may differ for hardware, the method may include recording, with respect to a plurality of fastener holes for a given surgical hardware component, corresponding respective offset values. In turn, the respective offset values for the plurality of fastener holes may be used for fastener selection for each one of the plurality of fastener holes. In an embodiment, the recordation of the offset values for the various fastener holes may be recorded by, for example, a controller of a surgical instrument. In turn, the controller may include a computer-based system. The computer-based system may include a memory that stores instructions for configuring a processor to record the various offset values for the hardware.

DETAILED DESCRIPTION

Figure 1:
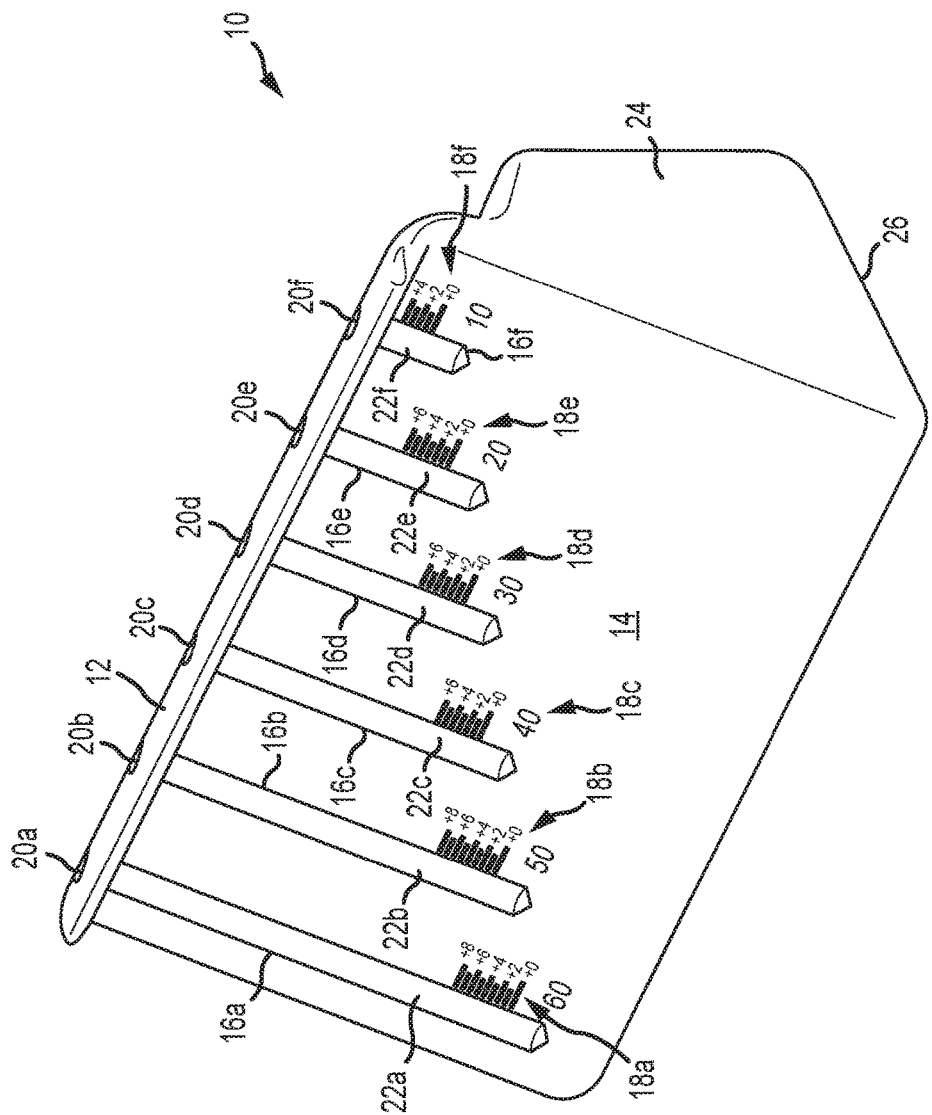
FIG. 1 depicts an embodiment of an offset reference guide.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope of the invention as defined by the claims.

With reference to FIGS. 1-5, an embodiment of an offset reference guide 10 is depicted. The offset reference guide 10 may include a reference surface 12. The offset reference guide further includes a gauge surface 14. The gauge surface 14 may extend relative to the reference surface 12. Furthermore, the gauge surface 14 is visible to the user of the guide. One or more fastener reliefs 16 may be provided that are configured to accept a fastener 60 for positioning the fastener 60 relative to the gauge surface 14 when the fastener is engaged with a surgical hardware component 50 in contact with the reference surface 12. In the embodiment depicted in FIGS. 1-5, a plurality of fastener reliefs 16a, 16b, 16c, 16d, 16e, and 16f may be provided. While six fastener reliefs 16 are provided in the embodiment of the guide 10 depicted in these figures, it may be appreciated that fewer or additional reliefs 16 may be provided without limitation. For instance, an alternative embodiment of an offset reference guide having a single fastener relief is discussed in greater detail below.

The gauge surface 14 may further include offset indicia 18 that are disposed on the gauge surface and positioned relative to each corresponding one of the fastener reliefs 16. The offset indicia 18 may be positioned on the gauge surface 14 relative to the reference surface 12 such that the offset indicia 18 may be alignable with a fastener 60 disposed in a fastener relief 16. Specifically, the hardware component 50 may be positioned in contacting relation with the reference surface 12. The fastener 60 may pass through a fastener hole 52 of the hardware component 50 and further into a fastener relief 16. In turn, upon alignment of the fastener 60 with the offset indicia 18, an offset value for the hardware component 50 may be determined. In this regard, the gauge surface 14 may comprise the offset indicia 18 such that the offset indicia 18 are arranged relative to the fastener relief 16 for use in determining an offset value for surgical hardware as described in greater detail below.

As stated above, the fastener reliefs are configured for receipt of a fastener therein. The fastener reliefs 16 may include a first portion 20 and a second portion 22. The first portion 20 may include a bore that extends a first distance from the reference surface 12. The second portion 22 may include a channel that may be continuous with at least a portion of the first portion 20 comprising the bore. The channel may extend a second distance from the reference surface 12. In this regard, the second distance may be greater than the first distance the bore extends from the reference surface 12.

Figure 2:
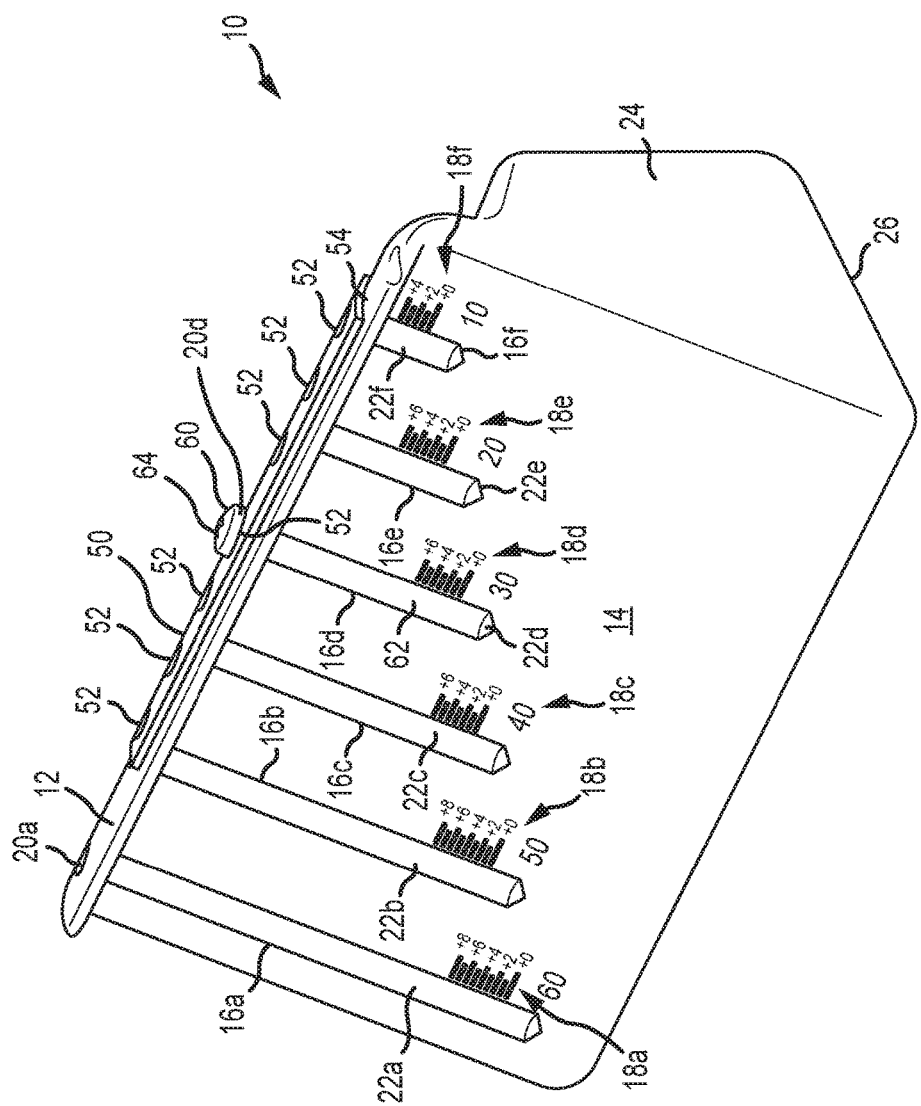
FIG. 2 depicts a front perspective view of an embodiment of an offset reference guide in relation to a surgical hardware component having a fastener positioned relative to the surgical hardware component and the offset reference guide.

With specific reference to FIG. 2, the fastener relief 16 may be configured to accept a fastener 60 therein. The first portion 20 may assist in alignment of the fastener relief 16 with a fastener hole 52 of a hardware component 50. The bore of the first portion 20 may be sized so as to receive the fastener 60 in close circumferential proximity to a cylindrical body of the fastener. In turn, the first portion 20 may be aligned with the fastener hole 52 of the hardware component 50 to receive a fastener 60 through the fastener hole 52 and the first portion 20 of the fastener relief 16.

The second portion 22 may provide a visual field for a user to observe the distal end portion 62 of the fastener 60 relative to the offset indicia 18 for the fastener relief 16. As such, the second portion 22 may comprise an at least partially open channel that provides visual access to a user of the distal end portion 62 of the fastener 60 when the fastener 60 is disposed in the fastener relief 16. As depicted in the embodiment of FIG. 2, the channel of the second portion 22 may comprise a recess in the gauge surface 14. In one embodiment, the channel may have a semicircular profile that generally corresponds to the cylindrical body of the fastener 60. For instance, the channel may be a semi-cylindrical channel that extends about at least a portion of the circumference of the cylindrical body of the fastener 60. As may be appreciated in FIG. 5, which shows a top view of the guide 10 allowing for viewing of the cross sectional profile of the fastener reliefs 16, the channel may be coaxial with the bore of the first portion 20. In this regard, at least a portion of the channel of the second portion 22 may comprise an extension of the profile of the bore of the first portion 20.

In a specific embodiment, the channel of the second portion 22 may extend about at least half of the circumference of the cylindrical body of the fastener 60. In still other embodiments, the channel of the second portion 22 may extend about a majority or even a majority of the circumference of the cylindrical body of the fastener 60. For instance, the channel of the second portion 22 may provide a slot through which the fastener 60 may be visible when disposed in the fastener relief 16. Such a slot may be provided in the gauge surface 14 such that the distal end portion 62 of the fastener 60 is visible in the fastener relief 16 in relation to the offset indicia 18.

Still further alternative embodiments of the fastener relief 16 may be provided. For instance, the fastener relief 16 may include a continuous bore with at least a portion of the bore being transparent or translucent such that a fastener 60 disposed in the fastener relief 16 may be visible to the user relative to the gauge surface 14 bearing the offset indicia 18. In this regard, the gauge surface 14 may include the offset indicia 18 provided relative to the translucent or transparent portions of the fastener relief 16 such that the distal end portion 62 of the fastener 60 may be visible in relation to the offset indicia 18.

In the embodiment depicted in FIGS. 1-5, the plurality of fastener reliefs 16 may each correspond to a known length of fastener. For example, fastener relief 16a may correspond to a known fastener length of 60 mm, fastener relief 16b may correspond to a known fastener length of 50 mm, fastener relief 16c may correspond to a known fastener length of 40 mm, fastener relief 16d may correspond to a known fastener length of 30 mm, fastener release 16e may correspond to a known fastener length of 20 mm, and fastener relief 16f may correspond to a known fastener length of 10 mm. In this regard, a fastener of any one of the known lengths may be utilized by selecting a corresponding one of the fastener reliefs 16 for use in determining an offset value for surgical hardware as will be described in greater detail below.

Figure 3:
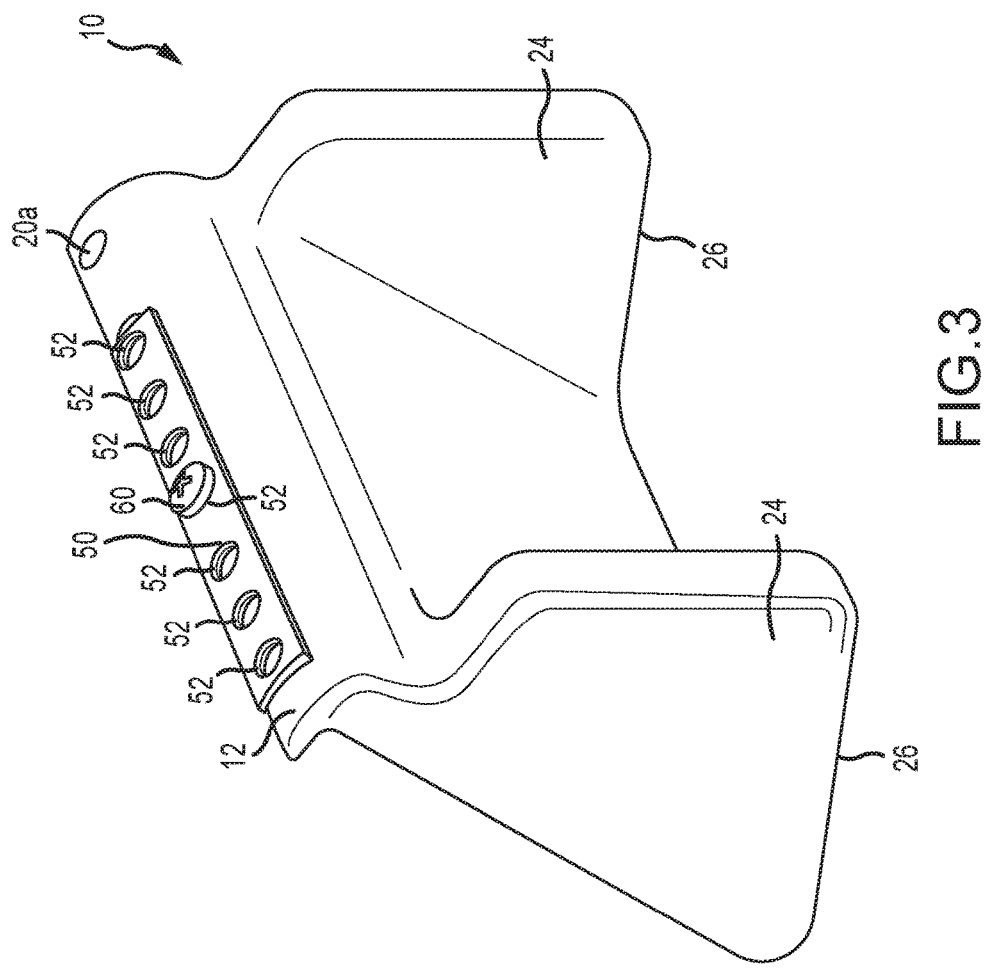
FIG. 3 depicts a rear perspective view of an embodiment of an offset reference guide in relation to a surgical hardware component having a fastener positioned relative to the surgical hardware component and the offset reference guide.

With continued reference to FIGS. 2-3, the offset reference guide 10 is depicted in relation to a surgical hardware component 50. Specifically, an interface surface 54 of the surgical hardware component 50 may be in contacting engagement with the reference surface 12. Furthermore, the surgical hardware component 50 may have a plurality of fastener holes 52 extending there through. In turn, at least one of the fastener holes 52 may be aligned with a fastener relief 16 (e.g., in the case depicted fastener relief 16d). In turn, an orthopedic fastener 60 may be disposed in the fastener hole 52 of the surgical hardware component 50 such that the fastener 60 extends relative to the fastener relief 16. That is, the fastener 60 may extend through the first portion 20 comprising the bore of the fastener relief 16. Furthermore, the fastener 60 may extend relative to the second portion 22 comprising the channel. As such, the distal end portion 62 of the fastener 60 may be disposed within the second portion 22 of the fastener relief 16. Specifically, the distal end portion 62 of the fastener 60 may be aligned in relation to the offset indicia 18.

Figure 4:
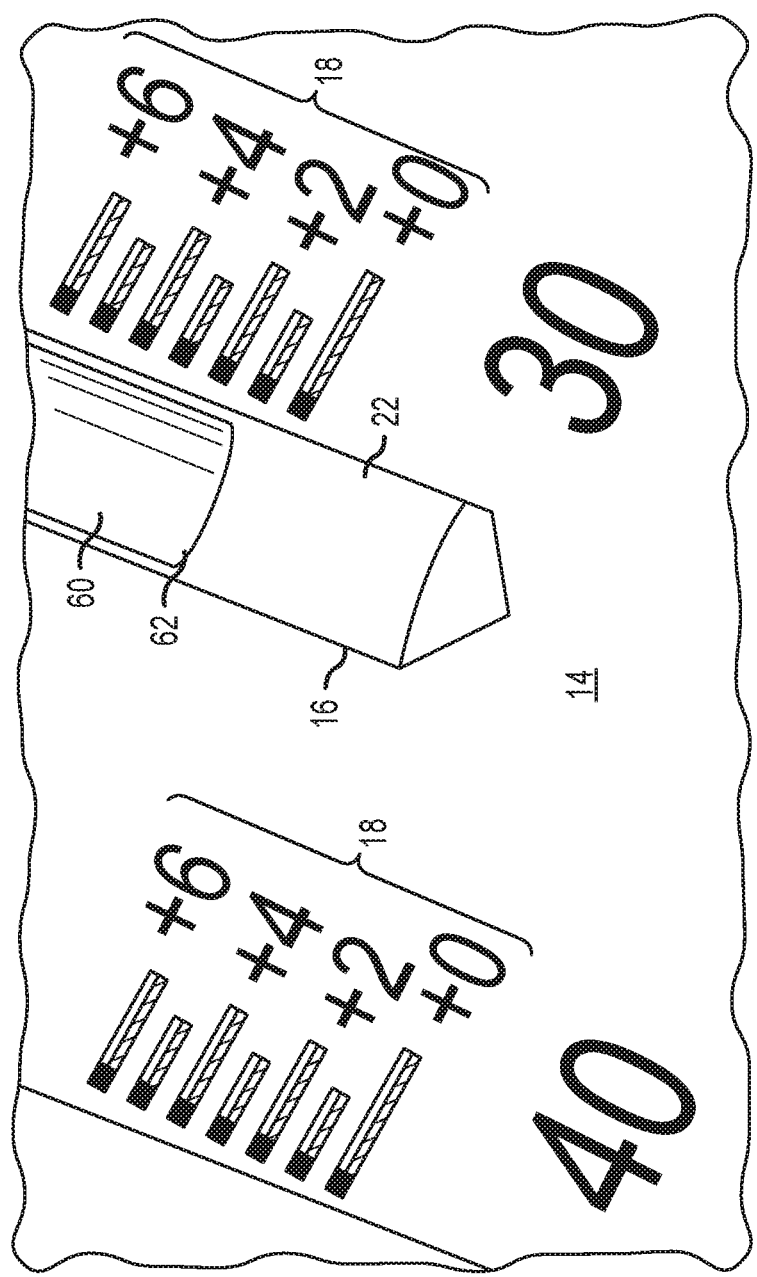
FIG. 4 depicts a detail view of an embodiment of offset indicia of an offset reference guide in relation to a fastener disposed relative thereto.
Figure 5:
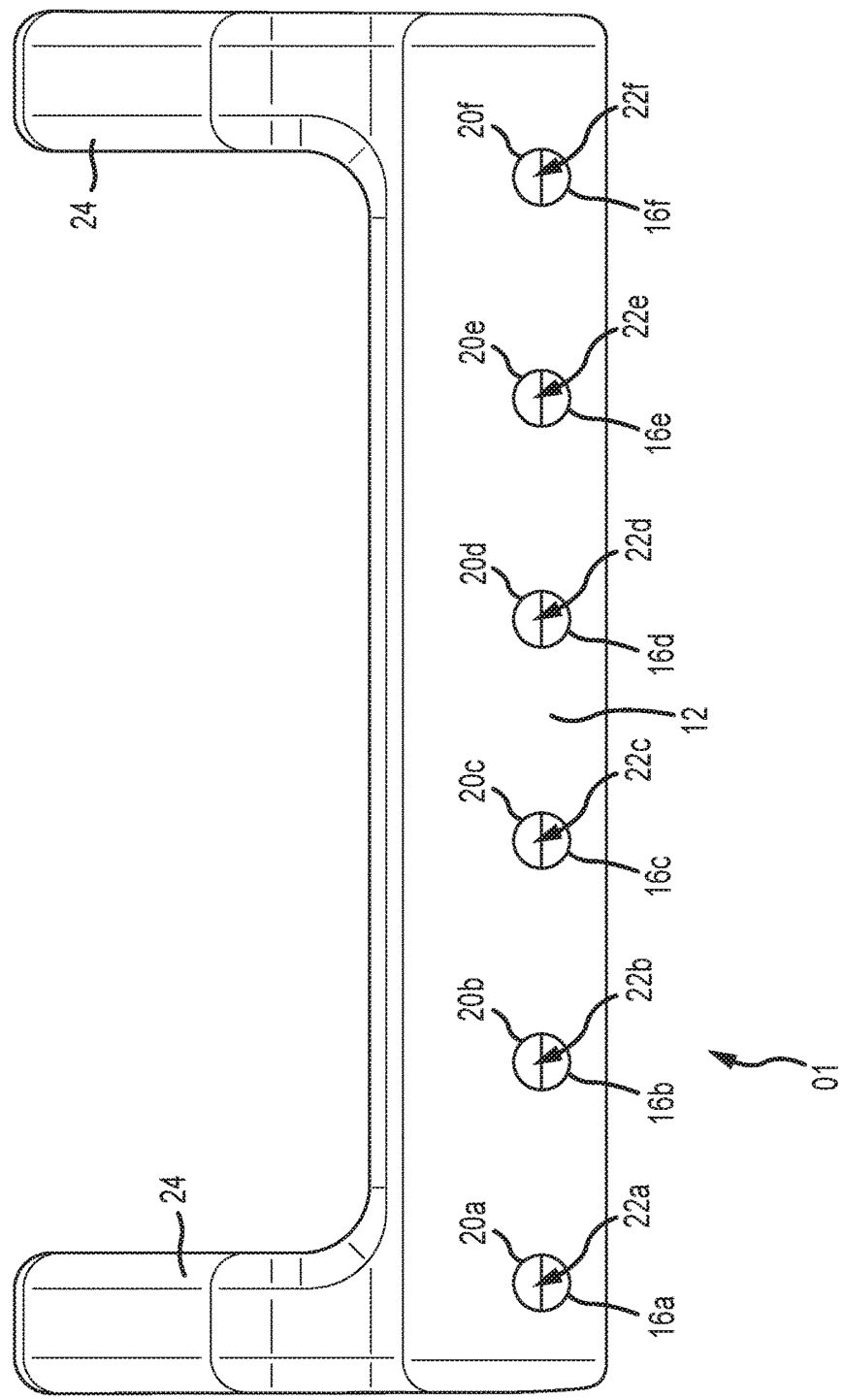
FIG. 5 depicts a top plan view of an embodiment of an offset reference guide.

In turn, with further reference to FIG. 4, which shows a detail view of the distal end portion 62 of a fastener 60 in relation to offset indicia 18 on the gauge surface 14, an offset value from the indicia 18 aligned with the distal end portion 62 of the fastener 60 that may be read from the gauge surface 14 of the guide 10. With returned reference to FIG. 2, it may be appreciated that the fastener 60 may be distally advanced such that it is seated relative to the fastener hole 52 of the surgical hardware component 50 in contacting engagement with reference surface 12. That is, the fastener hole 52 may comprise a contoured portion for accepting the fastener 60. For example, the fastener hole 52 may include a beveled or otherwise profiled surface that may at least partially provide a countersink for the fastener 60. In this regard, the fastener 60 may be fully seated in a distal position relative to the fastener hole 52 such that the distal end portion 62 of the fastener 60 may be in the most distal position relative to the surgical hardware 50. That is, the fastener 60 may be advanced as far as possible such that a head portion 64 of the fastener 60 is fully engaged with the fastener hole 52. In this fully distally seated position, the position of the fastener 60 may mimic the position the fastener 60 assumes when engaged with the bone of a patient.

In turn, by advancing the fastener 60 into a fully seated distal position, the accuracy of the offset value read from the gauge surface 14 may be improved. For instance, use of a traditional depth gauge for measurement of a bore with the hardware component 50 in place relative to the bone to determine a total bore length that accounts for the bone-to-bone measurement as well as the offset value of the hardware component 50 may not be feasible or practical. Initially, alignment of the components for such a measurement may be difficult to obtain in the context of a surgery. Moreover, as a depth gauge may present a different interface surface with the fastener hole 52 than the fastener head 62 presents, a true offset value may be difficult to obtain as a fastener 60 may reside at a different relative location relative to the fastener hole 52 than a depth gauge would when engaged with the hardware component 50. For instance, as described above, a fastener hole 52 of the hardware component 50 may include a bevel or profile (e.g., to allow for countersinking a fastener relative to the hardware component 50). As such, a depth gauge may not interface with the fastener hole 52 at the same level as the fastener engaged in the fastener hole 52. In turn, use of the offset reference guide 10 may provide an accurate measurement by replicating the interaction of the fastener 60 and the fastener hole 52 by seating the fastener 60 relative to the fastener hole 52.

Figure 6:
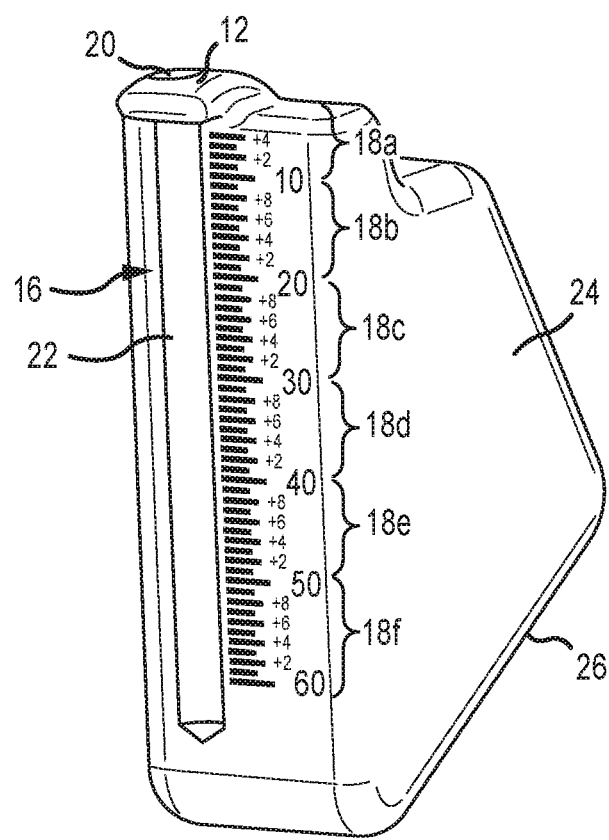
FIG. 6 depicts a front perspective view of an embodiment of an offset reference guide having a single fastener relief adapted for use with a plurality of different lengths of known fasteners.
Figure 7:
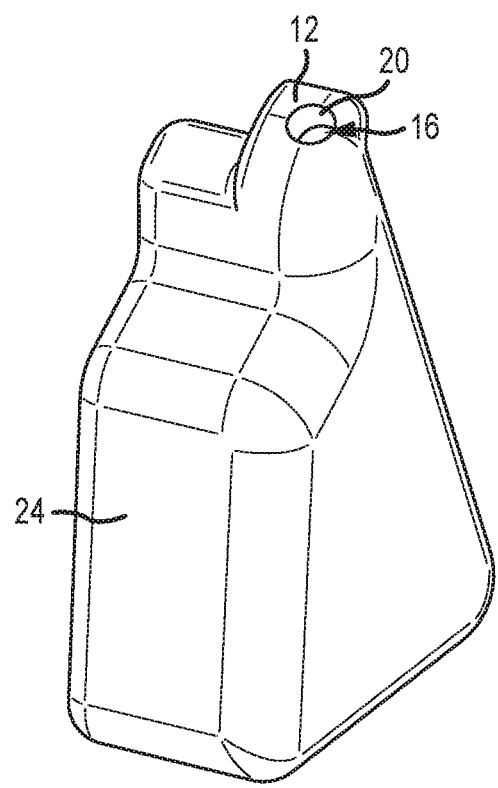
FIG. 7 depicts a rear perspective view of the embodiment of the offset reference guide of FIG. 6.

With further reference to FIGS. 6 and 7, another embodiment of an offset reference guide 10 is shown. In this embodiment, the offset reference guide 10 may include a fastener relief 16 with a structure similar to those described above in relation to the prior embodiment. However, the offset reference guide 10 shown in FIGS. 6 and 7 may comprise only a single fastener relief 16 provided with the offset reference guide 10. In this regard, the gauge surface 14 may comprise a plurality of offset indicia 18 each arranged relative to the single fastener relief 16. The single fastener relief 16 may receivingly accommodate different fastener lengths. As such, the plurality of offset indicia 18 may each correspond to a different known fastener length. For instance, in FIG. 6 offset indicia 18 are provided for a known fastener length of 10 mm in offset indicia 18a, 20 mm in offset indicia 18b, 30 mm in offset indicia 18c, 40 mm in offset indicia 18d, 50 mm in offset indicia 18e, and 60 mm in offset indicia 18f. As such, when determining the offset value for a hardware component 50, the corresponding offset indicia 18 for the known fastener length may be utilized to determine the offset value using the single fastener relief 16.

The use of the single fastener relief 16 may reduce the area of the reference surface 12. This may allow for the offset reference guide 10 to be used with more shapes and/or sizes of interface surfaces of hardware components 50. Specifically, the limited area of the reference surface 12 may allow for contact with a number of different hardware components 50 having varying profiles and/or configurations. Specifically, the reference surface 12 may extend relative to the opening of the first portion 20 of the fastener relief 16 corresponding to a bore. The reference surface area 12 may be limited to an area immediately adjacent to the terminal end portion of the fastener relief 16. The reference surface 12 may extend for a limited distance (e.g., a distance equal to or less than 50% of the bore diameter, a distance equal to or less than 100% of the bore diameter, a distance equal to or less than 150% of the bore diameter, or a distance equal to or less than 200% of the bore diameter).

Figure 8:
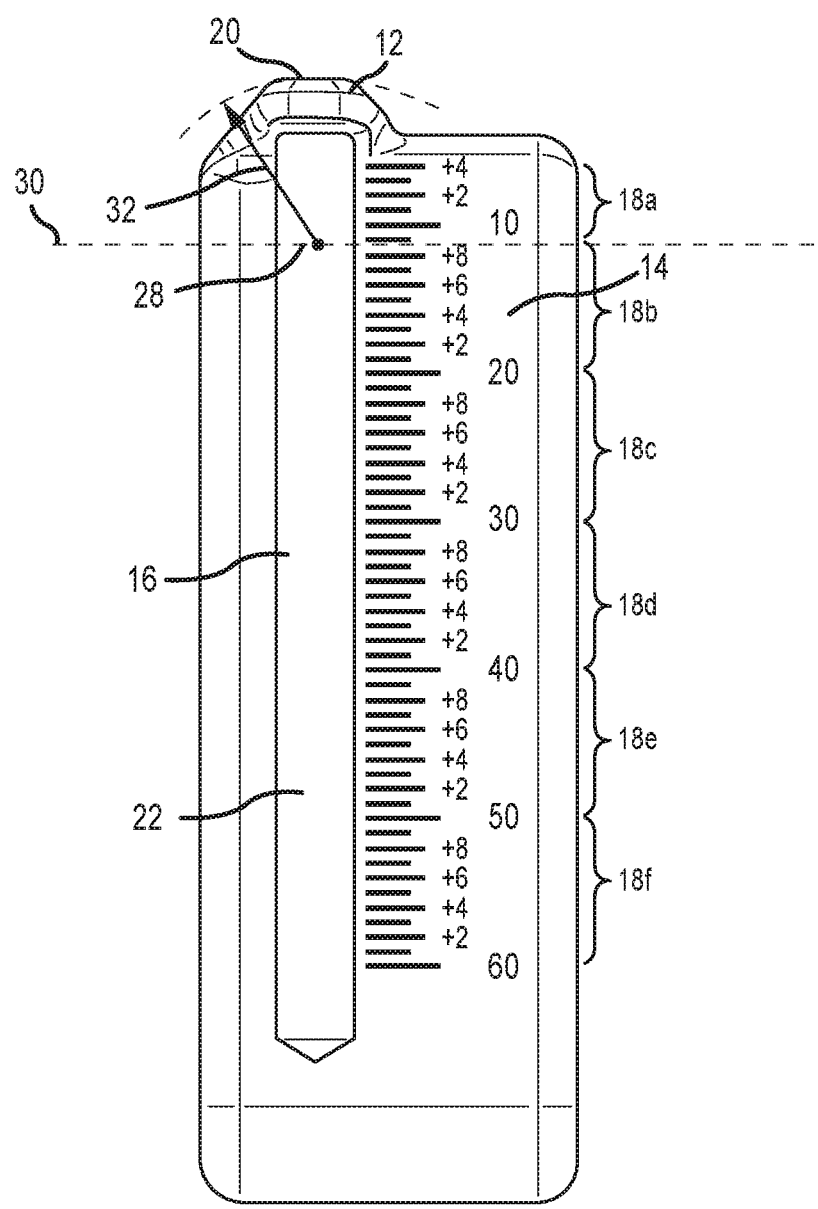
FIG. 8 depicts a front plan view of an embodiment of an offset reference guide.

In addition to the limited area of the reference surface 12, the reference surface 12 may have a profile that promotes intimate contact between an interface surface 54 of a hardware component 50 and the reference surface 12. For instance, the profile or contour of the reference surface 12 may have a radius of curvature relative to at least one axis that is orthogonal to a central axis of the fastener relief 16. For instance, in FIGS. 8 and 9, a first axis 28 is shown that has a corresponding first radius of curvature 32 defining a profile of the reference surface 12 in a direction generally corresponding to the width of the reference surface 12. As may also be appreciated from FIGS. 8 and 9, a second axis 30 may be provided that is orthogonal to both the first axis 28 and the central axis of the fastener relief 16. A corresponding second radius of curvature 34 may be provided relative to the second axis 30. In this regard, the reference surface 12 may have a three dimensional profile created by the combination of the first radius of curvature 32 and the second radius of curvature 34. While the first axis 28 and second axis 30 are depicted as intersecting, thus depicting the first radius of curvature 32 and the second radius of curvature 34 being equal in length, in some embodiments, the radius of curvatures 32 and 34 may differ. In this regard, while the axes 28 and 30 may be orthogonal to one another and the central axis of the fastener relief, they need not intersect and can be provided at different relative locations to the reference surface 12 to define different radiuses of curvature 32 and 34. Additionally, while the contoured reference surface 12 is described in relation to the embodiment depicted in FIGS. 8 and 9 having a single fastener relief 16, it may be appreciated that such a contoured reference surface 12 having a radius of curvature relative to a plurality of axes may be provided with each or any of the plurality of fastener reliefs 16 of the embodiment depicted in FIGS. 1-5.

Figure 10:
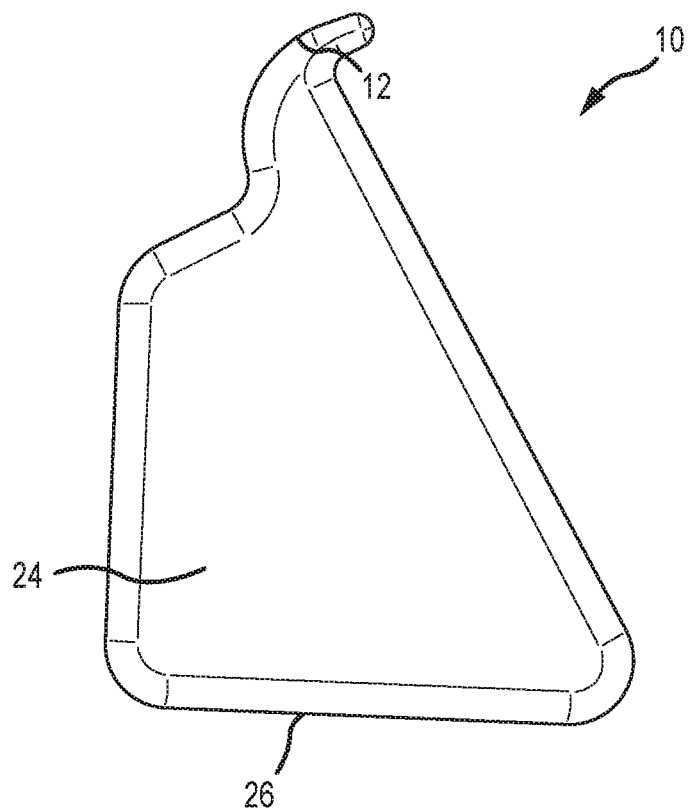
FIG. 10 depicts a side plan view of an embodiment of an offset reference guide.
Figure 11:
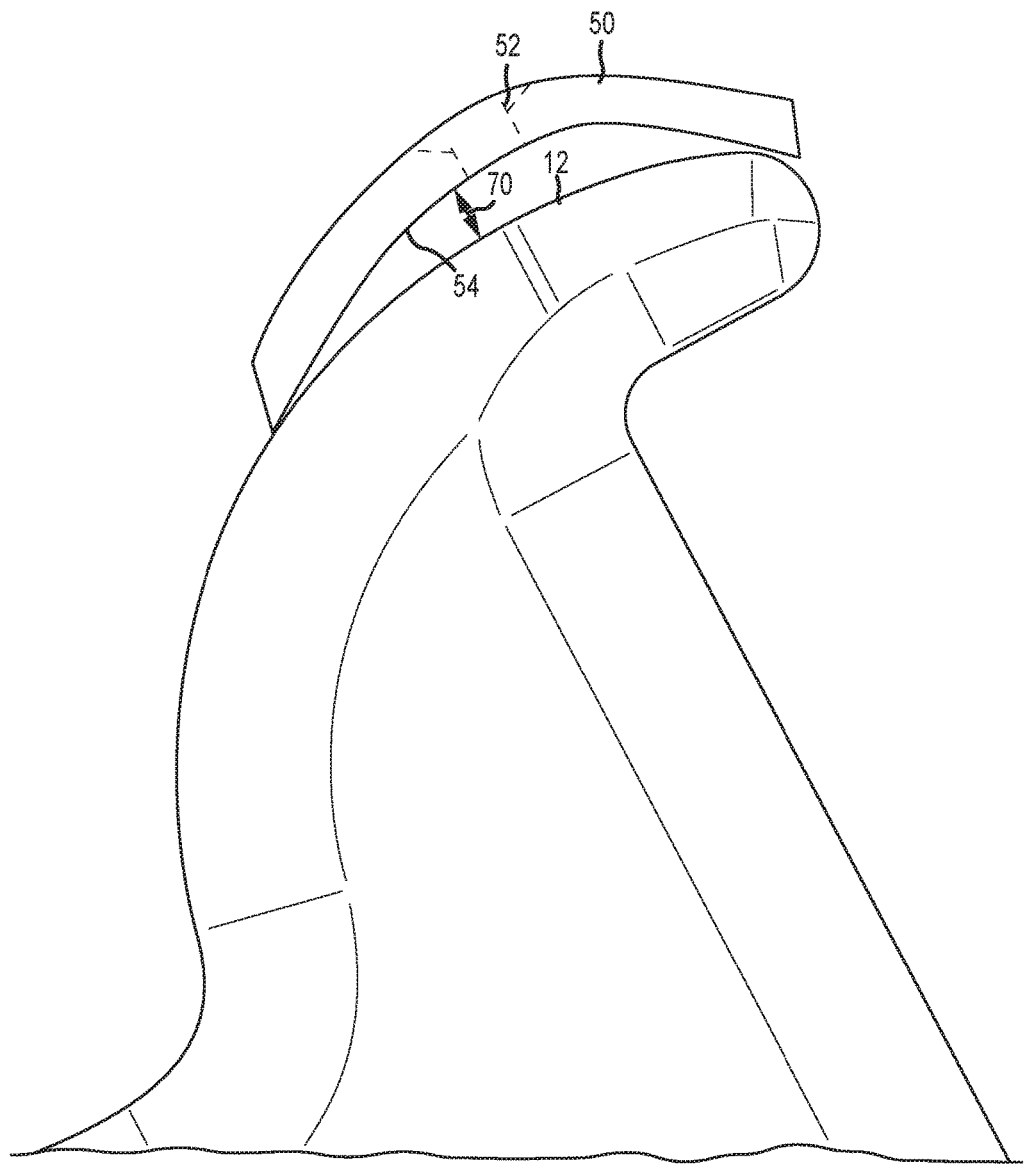
FIG. 11 depicts a detailed side plan view of an embodiment of a reference surface of an offset reference guide in relation to a surgical hardware component having a radius of curvature less than that of the radius of curvature of the reference surface.

As such, in relation to any of the foregoing embodiments, the reference surface 12 may be in intimate contact with the interface surface 54 of the surgical hardware component 50. With further reference to FIG. 10, a reference surface 12 is shown in side profile. As may be appreciated, the reference surface 12 may comprise a radius of curvature. The radius of curvature of the reference surface 12 may be less than a radius of curvature of the surgical hardware component 50 engaged with reference surface 12. Specifically, the radius of curvature of the reference surface 12 may be less than a radius of curvature of the interface surface 54 of the hardware component 50 to assist in providing direct contacting engagement adjacent to the first portion 20 of the fastener relief 16 and the fastener hole 52 of the hardware component 50. For example, as shown in FIG. 11, a surgical hardware component 50 having a radius of curvature along the interface surface 54 thereof may be less than a radius of curvature of the reference surface 12. In turn, the interface surface 54 may be bridged or separated from the reference surface 12 by a distance 70. That is, the gapping or bridging may occur from the radius of curvature of the interface surface 54 of the surgical hardware component 50 being less than a radius of curvature of the reference surface 12.

Figure 12:
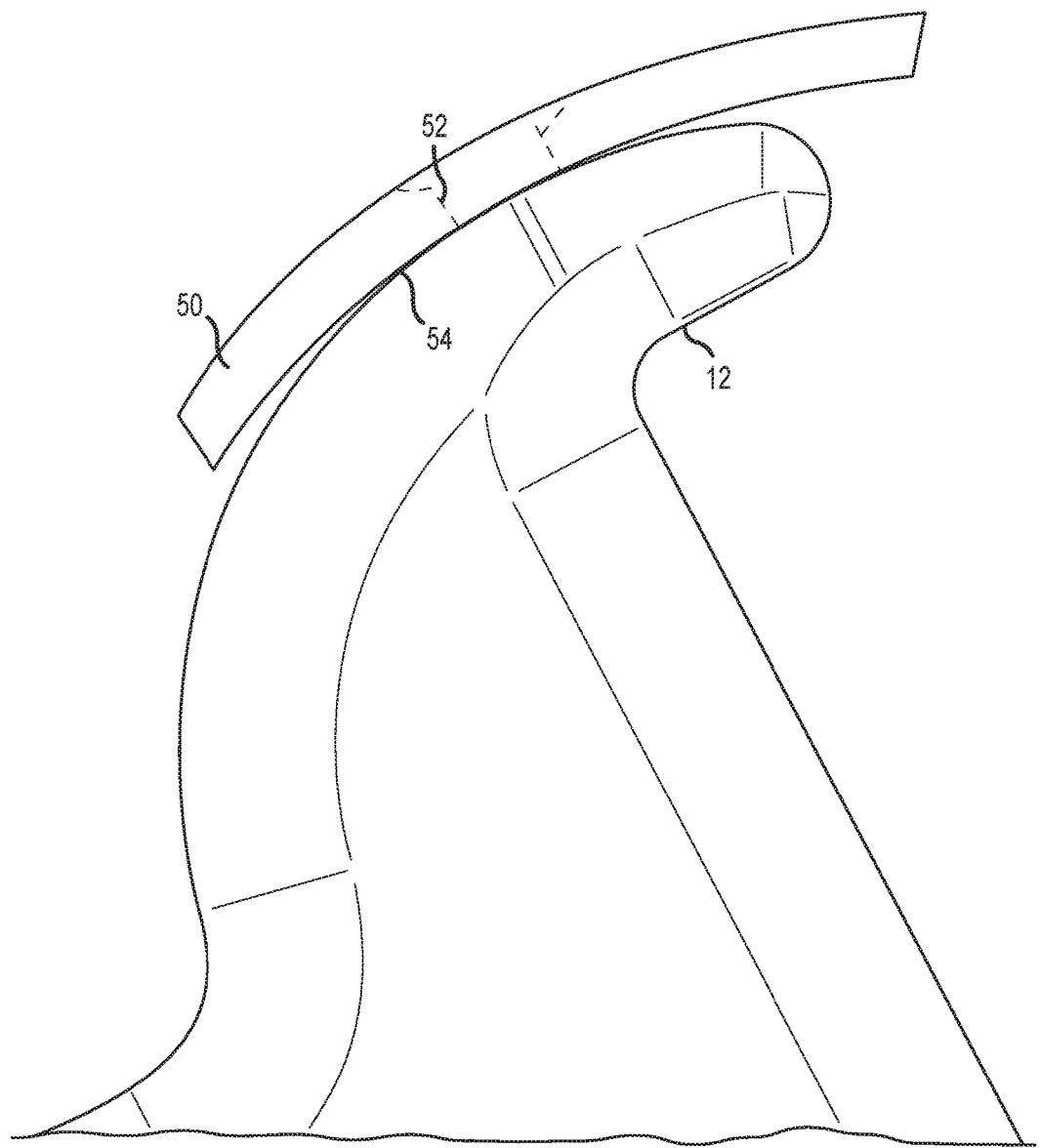
FIG. 12 depicts a detailed side plan view of an embodiment of a reference surface of an offset reference guide in relation to a surgical hardware component having a radius of curvature greater than that of the radius of curvature of the reference surface.
Figure 13:
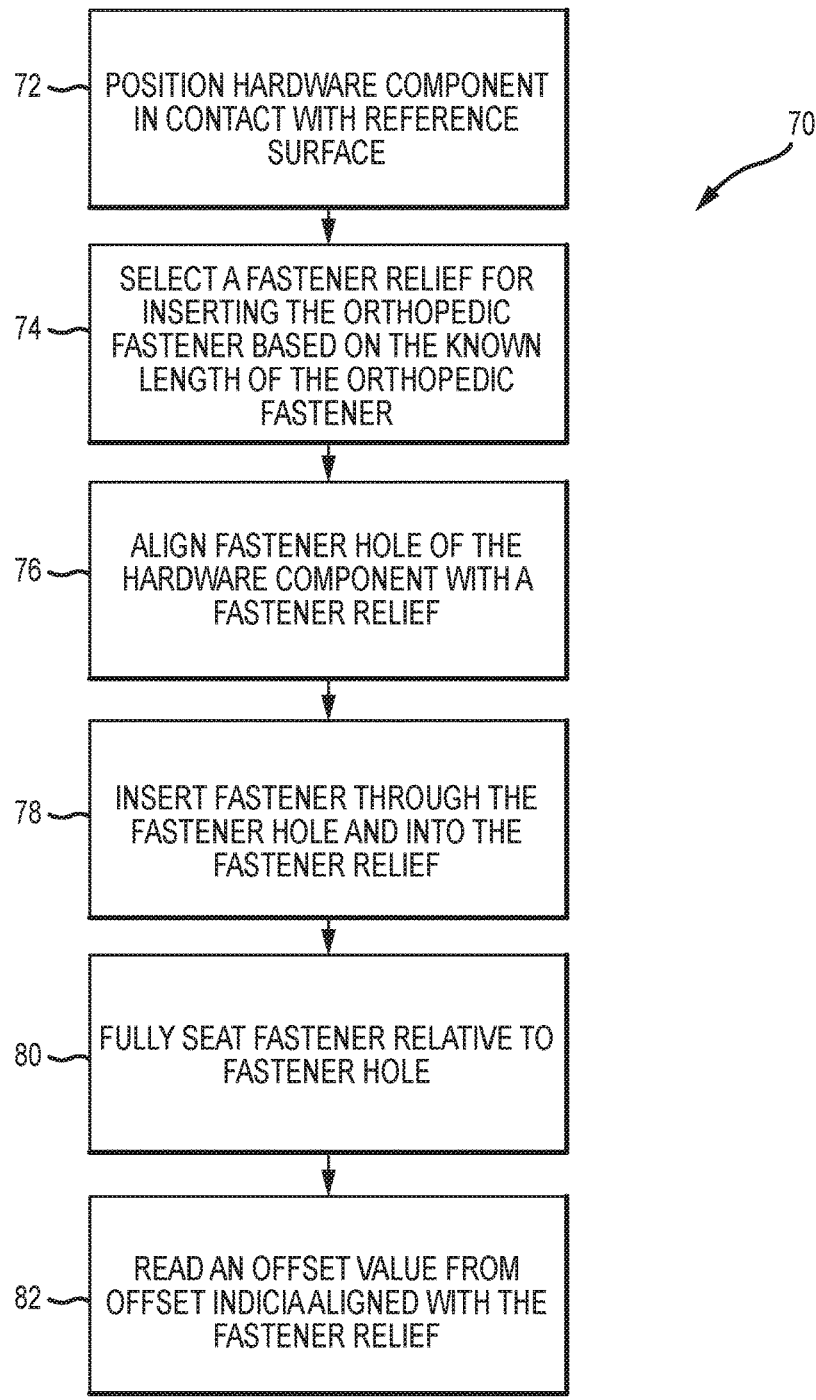
FIG. 13 is a flowchart representing an embodiment of a method for use of an offset reference guide to determine an offset value for surgical hardware.
Figure 14:
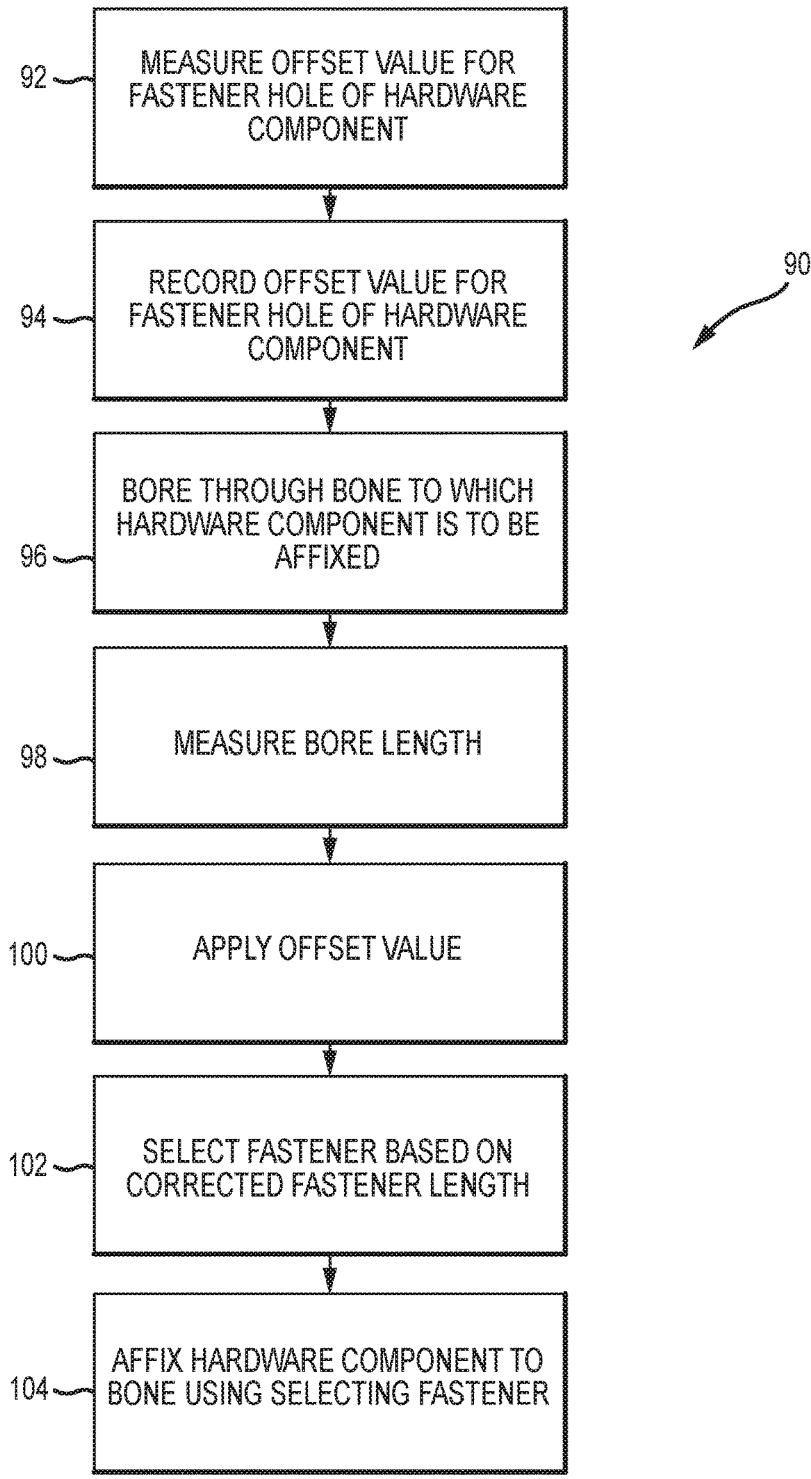
FIG. 14 is a flowchart representing an embodiment of a method for use of an offset value in affixing surgical hardware to a bone.

In contrast, with further reference to FIG. 12, the surgical hardware component 50 is depicted where the interface surface 54 has a radius of curvature larger than the radius of curvature of the reference surface 12. In this regard, the interface surface 54 of the surgical hardware component 50 may be in intimate contact adjacent to where the fastener hole 52 engages the fastener relief 16 of the gauge 10. The foregoing discussion of the radius of curvature of the reference surface 12 relative to the interface surface 54 may hold true for any contour of the reference surface 12 (i.e., even when multiple radiuses of curvature or other profiles are provided for the reference surface 12).

Furthermore, the offset reference guide 10 may comprise grip portions 24. With returned reference to FIG. 3, the grip portions 24 may include fin structures that extend relative to the gauge surface 14. In this regard, the grip portions 24 may comprise structures that may be grasped by a user when handling the offset reference guide 10. Specifically, the grip portions 24 may be disposed adjacent to opposite ends of the offset reference guide 10.

Furthermore, the grip portions 24 may comprise a support portion 26 that may allow for the offset reference guide 10 to be supportably engaged by surface. Specifically, the support portions 26 may be angled in relation to the gauge surface 14 such that the gauge surface 14 is angled for better viewing by a user when the offset reference guide 10 is supported by surface. A similar support portion 26 may be provided in the embodiments depicted in FIGS. 6-9 where the offset reference guide 10 shown in those figures also has a grip portion 24 extending relative to the gauge surface 14.

With further reference to FIG. 11, a method 70 for use of an offset reference guide is depicted as a flowchart. The method 70 may begin by positioning 72 a hardware component 50 relative to a reference surface 12 of a guide 10. Specifically, an interface surface 54 of the hardware component 50 adapted for engagement of a bone to which the hardware component 50 is to be affixed may be disposed in contacting engagement with the reference surface 12. In turn, the method 70 may, in the case of a guide 10 with a plurality of fastener reliefs 16, include selecting 74 a fastener relief 16 that corresponds to a known fastener length for an orthopedic fastener 60. In turn, the method 70 may include aligning 76 a fastener hole 52 of the hardware component 50 with the selected fastener relief 16.

The method 70 may also include inserting 78 the fastener 60 though the fastener hole 52 such that the fastener 60 extends into the fastener relief 16. The method 70 may include fully seating 80 the fastener 60 relative to the fastener relief 16. As described above, this may mimic the positioning of the fastener 60 relative to the hardware component 50 when affixed to the bone. Upon fully seating 80 the fastener 60 relative to the fastener hole 52 of the hardware component 50, a distal end portion 62 of the fastener 60 may be disposed relative to the offset indicia 18 on the gauge surface 14. In turn, the method 70 may include reading 82 an offset value from the offset indicia 18 with which the distal end portion 62 of the fastener 60 is aligned.

Figure 9:
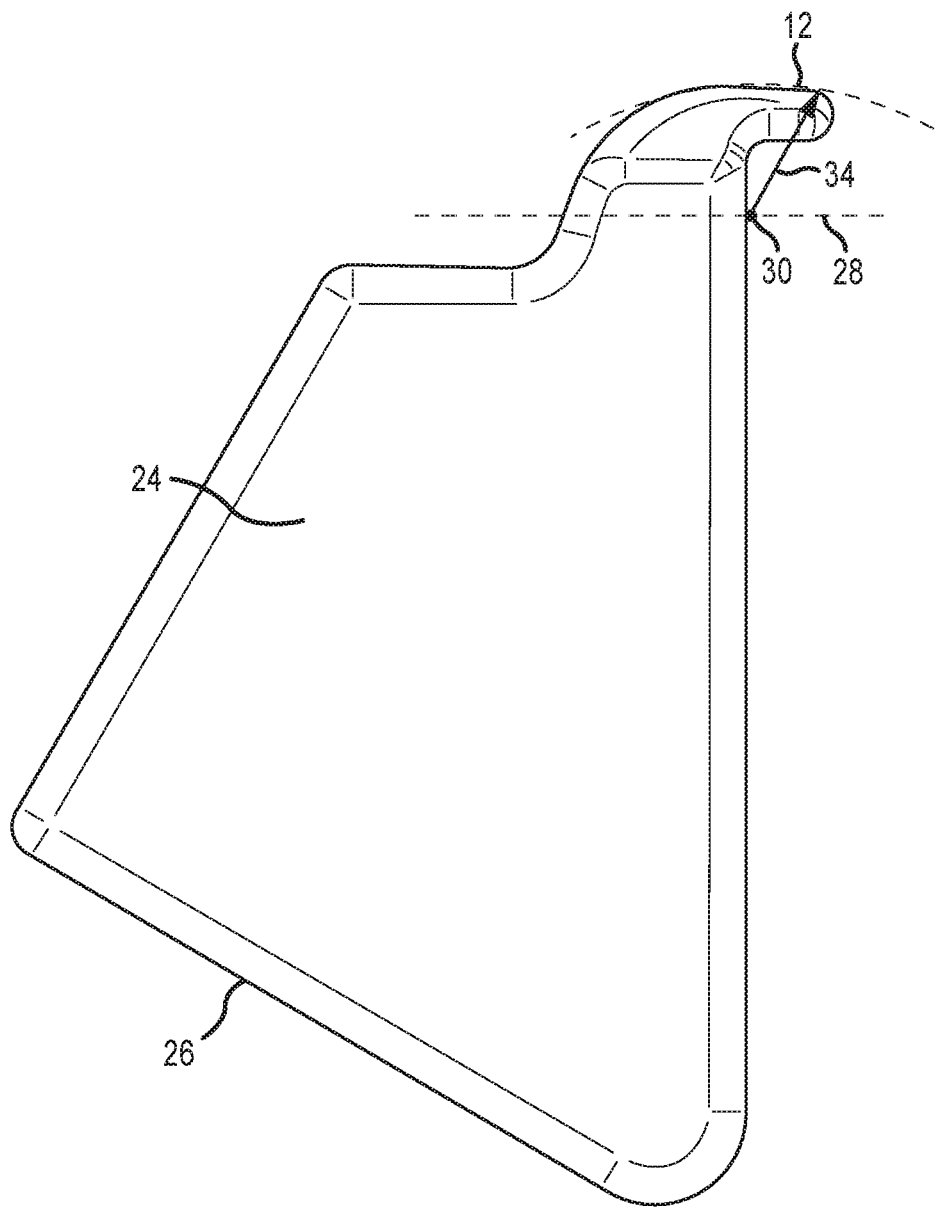
FIG. 9 depicts a side plan view of an embodiment of an offset reference guide.

FIG. 12 depicts a method 90 for use of an offset value (e.g., as determined by the method 70 depicted in FIG. 9). The method 90 may include measuring 92 an offset value for a hardware component 50 (e.g., using the method 70). The method 90 may also include recording 94 the offset value for a fastener hole 52 of a hardware component 50. The recording 94 may include use of a computer-based system for recording the offset value. For instance, a user interface may be provided in conjunction with, for example, an instrument used in boring a hole in a bone to which the hardware component 50 is to be affixed. The user interface of the instrument may be executed by a processor in operative communication with a memory that stores instructions for configuring the processor. The memory may also include information regarding a particular hardware component 50 (e.g., including the number and/or arrangement of fastener holes 52 for a hardware component 50). In turn, the computer-based system may be operative to assist in tracking recordation of the offset values for various fastener holes 52 and/or calculation of corrected fastener lengths determined using an offset value.

The method 90 may further include boring 96 through a bone to which the hardware component 50 is to be affixed. The method 90 further includes measuring 98 the resulting bore length. In at least one embodiment, the boring 96 and measuring 98 may be completed in a single operation using, for example, a drill having a measurement system integrated therewith such as those described in the disclosures incorporated by reference above. In any regard, upon measurement 98 of the bore length and measurement 92 of the offset value, the offset value may be applied 100 to the measured bore length to determine a corrected fastener length. In turn, the method 90 may include selecting 102 a fastener based on the corrected fastener length based on the measured 98 bore length and the measured 92 offset value. The method 90 may also include affixing 104 the hardware component 50 to the bone through which the hole is bored through. The affixing 104 may include use of the selected fastener having a length corresponding to the corrected fastener length determined based on the bore length and the offset value.

Accordingly, as described above, using the apparatuses and methods described herein, an offset value for a hardware component may be determined. As such, measurements using measurement devices may be corrected and/or verified for a hardware component having an offset value. In turn, even in the context of a kit whereby the hardware component, fastener, depth gauge, and/or other components are calibrated for coordinated use, determination of the offset value may allow for independent use of components external to a provided kit. Furthermore, even in the absence of a kit, determination of an offset value may provide more accurate fastener selection. Specifically, as the offset value may be measured based on actual interaction of a fastener in relation to a fastener hole of a hardware component, an accurate determination of fastener length may be provided.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. An offset reference guide for use in determining offset values for orthopedic surgical hardware, the guide comprising:

a reference surface adapted to contactably engage a surgical hardware component at an interface surface of the surgical hardware component;

a gauge surface extending relative to the reference surface, wherein the gauge surface is visible to a user of the guide;

a fastener relief extending from the reference surface and relative to the gauge surface, the fastener relief being configured to receive and index an orthopedic fastener relative to the reference surface and the gauge surface when the orthopedic fastener is disposed through a surgical hardware component disposed at the reference surface; and offset indicia disposed on the gauge surface and aligned with the fastener relief, wherein the offset indicia are indicative of an offset to a know fastener length relative to the fastener relief.

2. The offset reference guide of claim 1, wherein a first portion of the fastener relief comprises a bore extending along at least a terminal end portion of the fastener relief adjacent to the reference surface, wherein the bore is sized to receive the orthopedic fastener therein.

3. The offset reference guide of claim 2, wherein a second portion of the fastener relief comprises a channel having an open portion along at least a portion of the gauge surface such that the fastener is visible relative to the gauge surface along the second portion.

4. The offset reference guide of claim 1, wherein the reference surface is radiused relative to a terminal end portion of the fastener relief.

5. The offset reference guide of claim 4, wherein a radius of curvature of the reference surface is less than the radius of curvature of an interface surface of a surgical hardware component disposed at the reference surface.

6. The offset reference guide of claim 1, wherein the reference surface is contoured about the terminal end portion of the fastener relief such that the reference surface comprises a first and second radius of curvature relative to two axes, respectively, that are each orthogonal to the fastener relief.

7. The offset reference guide of claim 6, wherein the first and second radiuses of curvature are different.

8. The offset reference guide of claim 1, further comprising a plurality of fastener reliefs, each extending from the reference surface and relative to the gauge surface, wherein the plurality of fastener reliefs each extend a different distance along the gauge surface.

9. The offset reference guide of claim 8, wherein each of the plurality of fastener reliefs correspond to a different known fastener length such that each of the plurality of fastener reliefs include a corresponding offset indicia for the corresponding known fastener length of the given fastener relief.

10. The offset reference guide of claim 1, wherein a plurality of offset indicia each corresponding to a different known fastener length are disposed relative to the fastener relief.

11. The offset reference guide of claim 10, wherein only one fastener relief is provided.

12. The offset reference guide of claim 1, further comprising grip portions extending relative to the gauge surface.

13. The offset reference guide of claim 12, wherein the grip portions are disposed at opposite end portions of the offset reference guide.

14. The offset reference guide of claim 13, wherein the grip portions comprise fins extending from a rear surface of the offset reference guide.

15. The offset reference guide of claim 14, wherein the grip portions comprise support structures disposable on a surface, wherein the support structures orient the gauge surface at an angle relative to the surface for viewing by a user of the offset reference guide.

16. A method for use of an offset reference guide in determining offset values for orthopedic surgical hardware, comprising:

positioning an interface surface of a surgical hardware component in contact with a reference surface of the offset reference guide;

aligning a fastener hole of the surgical hardware component with a fastener relief of the offset reference guide;

inserting an orthopedic fastener of a known length through the fastener hole of the surgical hardware component relative to the fastener relief to dispose the orthopedic fastener relative to a gauge surface along which the fastener relief extends;

reading an offset value from offset indicia disposed on the gauge surface and aligned with the fastener relief, wherein the offset value corresponds to a given one of the offset indicia with which a distal end of the orthopedic fastener is aligned when disposed in the fastener relief.

17. The method of claim 16, further comprising:

selecting, from a plurality of fastener reliefs each corresponding to a different respective known fastener length, a given fastener relief for inserting the orthopedic fastener based on the known length of the orthopedic fastener.

18. The method of claim 16, further comprising:

measuring a measured bore length of a drilled hole through a bone to which the surgical hardware is to be affixed;

adding to the measured bore length the offset value to obtain a corrected fastener length; and selecting a fastener based on the corrected fastener length.

19. The method of claim 16, wherein the inserting further comprises fully distally seating the orthopedic fastener in the fastener relief relative to the surgical hardware.

20. The method of claim 16, further comprising:

recording, with respect to a plurality of fastener holes for a given surgical hardware component, corresponding respective offset values.

* * * * *